United States Patent [19]

Yehl et al.

[11] Patent Number: 5,043,840
[45] Date of Patent: Aug. 27, 1991

[54] APPARATUS AND METHOD FOR SELECTIVE ENVIRONMENTAL CONDITIONING OF SUBSTANTIALLY ENCLOSED AREAS

[75] Inventors: James E. Yehl; Rex R. Coppom, both of Boulder, Colo.

[73] Assignee: American Environmental Systems, Inc., Boulder, Colo.

[21] Appl. No.: 300,121

[22] Filed: Jan. 23, 1989

Related U.S. Application Data

[63] Continuation-in-part of Ser. No. 138,143, Dec. 28, 1987, Pat. No. 4,911,737.

[51] Int. Cl.⁵ .............................................. H05F 3/06
[52] U.S. Cl. ..................................... 361/231; 361/216
[58] Field of Search ............... 361/213, 216, 231, 235; 55/2, 124, 131, 138, 139, 154; 98/2.11

[56] References Cited

U.S. PATENT DOCUMENTS

| | | | |
|---|---|---|---|
| Re. 27,027 | 1/1971 | Cristofu et al. | 361/231 |
| 3,583,754 | 6/1971 | von Berckhelm | 55/2 |
| 3,678,337 | 7/1972 | Grauvogel | 361/231 |
| 3,711,743 | 1/1973 | Bolasny | 361/231 |
| 3,887,846 | 6/1975 | von Beckhelm | 361/231 |
| 4,271,452 | 6/1981 | Lee | 361/231 |
| 4,542,434 | 9/1985 | Gehlke et al. | 361/231 |
| 4,757,421 | 7/1988 | Mykkaren | 361/231 |
| 4,811,159 | 3/1989 | Foster, Jr. | 361/231 |
| 4,907,498 | 3/1990 | Haute | 361/231 |
| 4,911,737 | 3/1990 | Yehl et al. | 361/231 |

Primary Examiner—A. D. Pellinen
Assistant Examiner—Jeffrey A. Gaffin
Attorney, Agent, or Firm—Harold A. Burdick

[57] ABSTRACT

An apparatus and method for selective environmental conditioning of a substantially enclosed utilization area is disclosed for removal of undesired matter therefrom while more readily establishing predetermined naturally occurring environmental characteristics therein. The apparatus includes negative ion generators and positive electrostatic field generators positioned relative to each other so that the field generators are adjacent to, and spaced a preselected distance from, the ion generators to enhance more even distribution of the positive electrostatic field and negative ions within the enclosed area and particularly adjacent to units and structural surfaces, such as walls, work surfaces, people, equipment, and the like in the area. The electrostatic field generators include field collectors and pulse generating circuitry for generating pulsations of selected frequency within the positive electrostatic field, and the apparatus includes control means for selectively controlling ion output, field strength and field pulsation frequency.

17 Claims, 8 Drawing Sheets

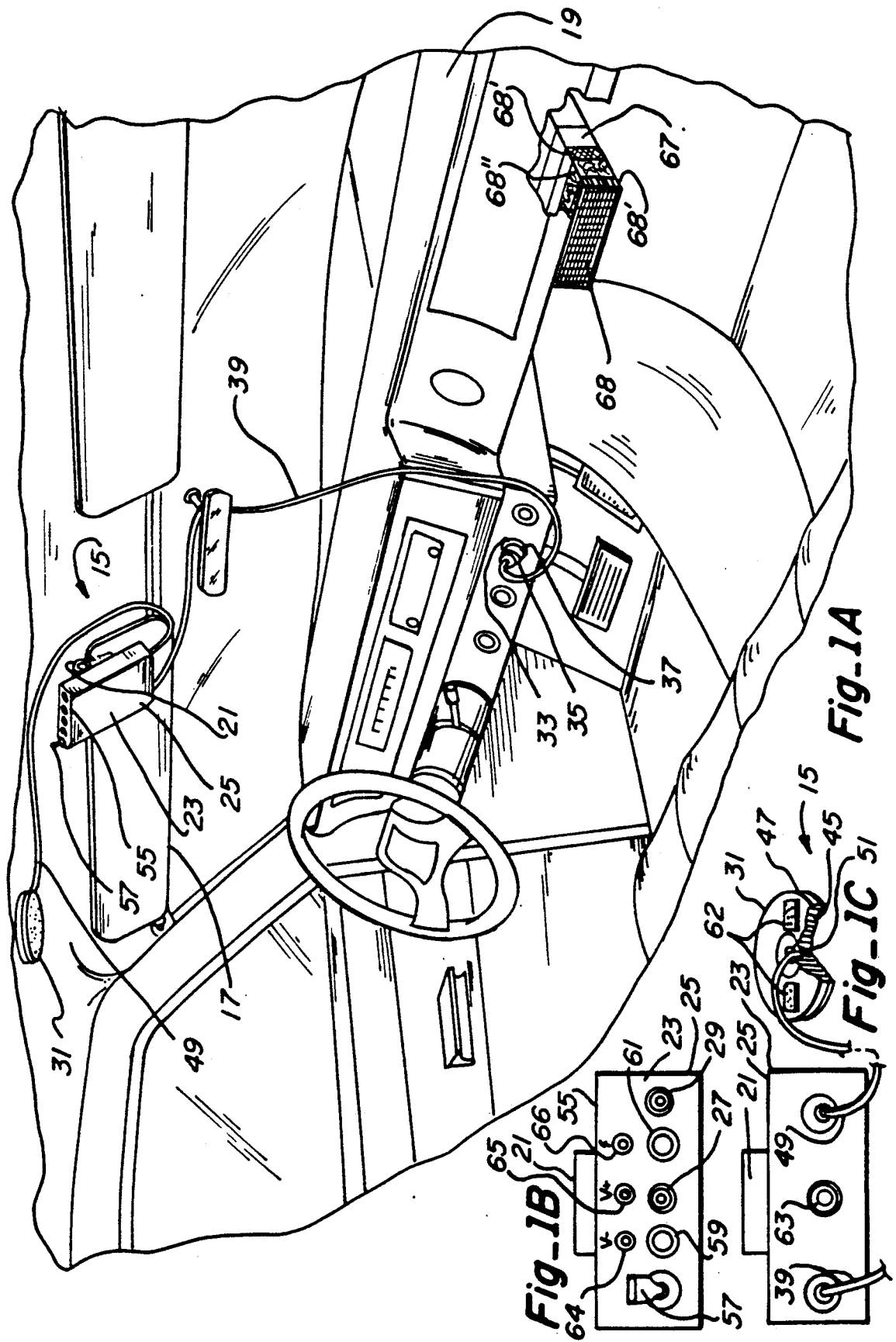

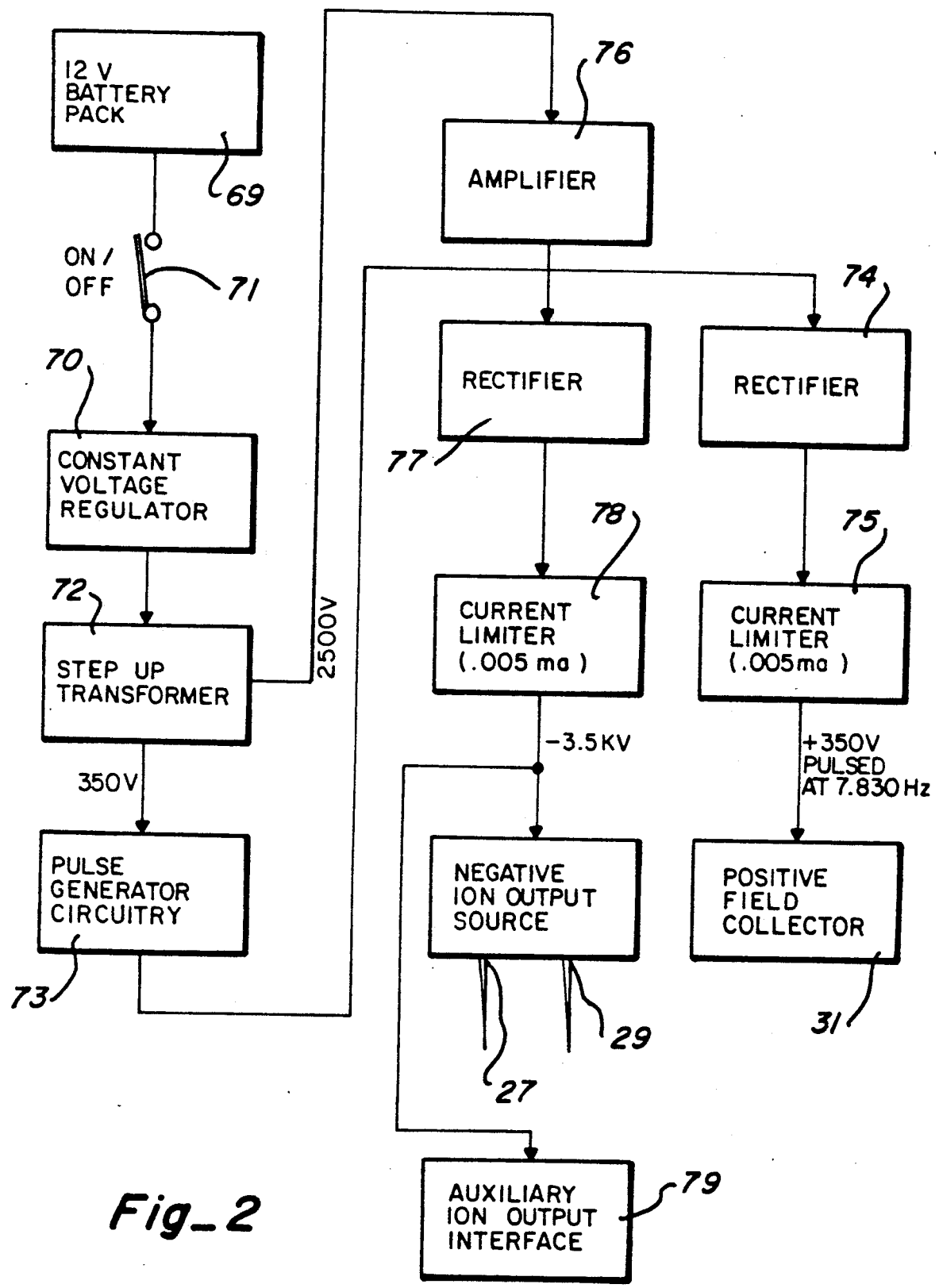
Fig_2

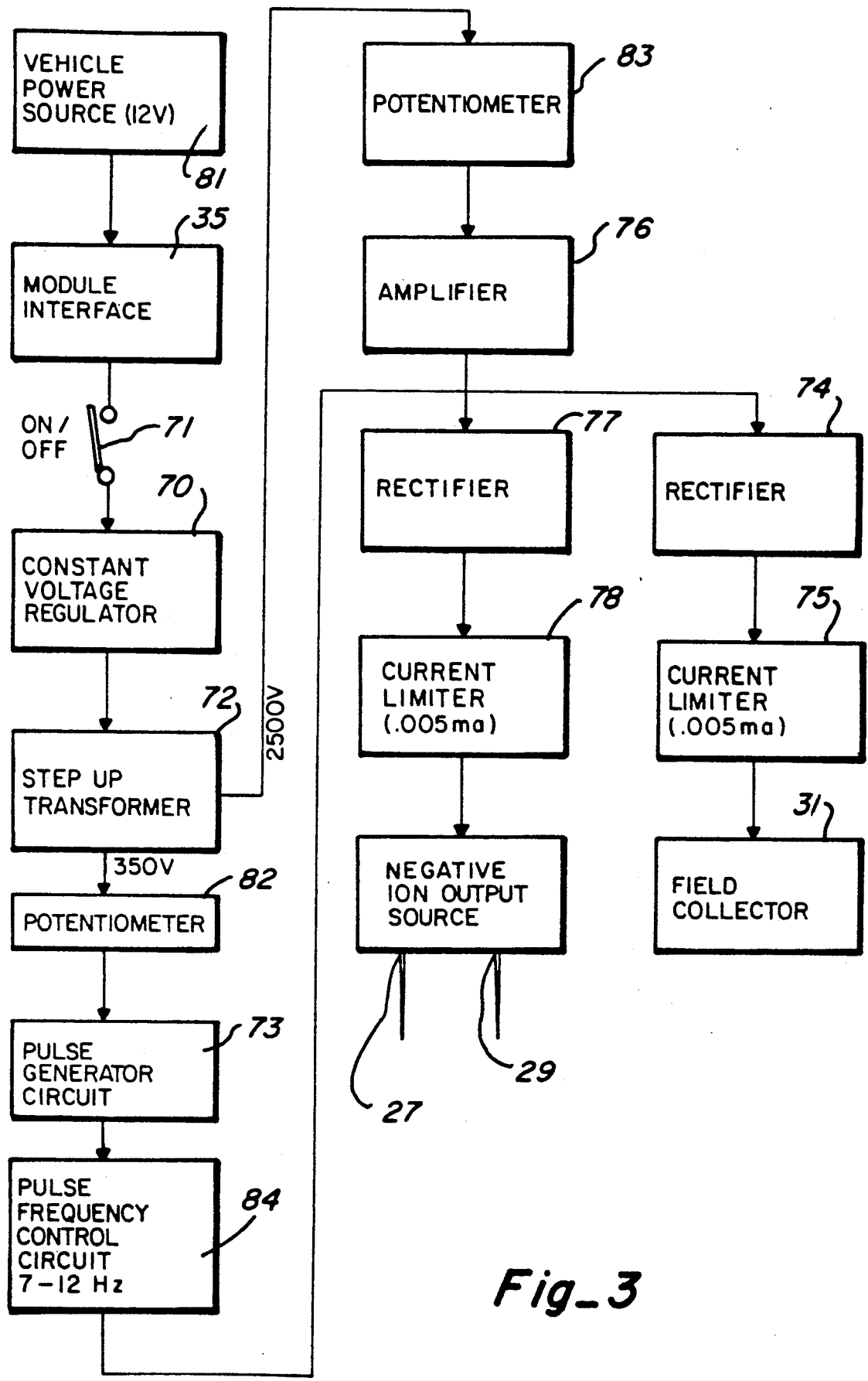
Fig_3

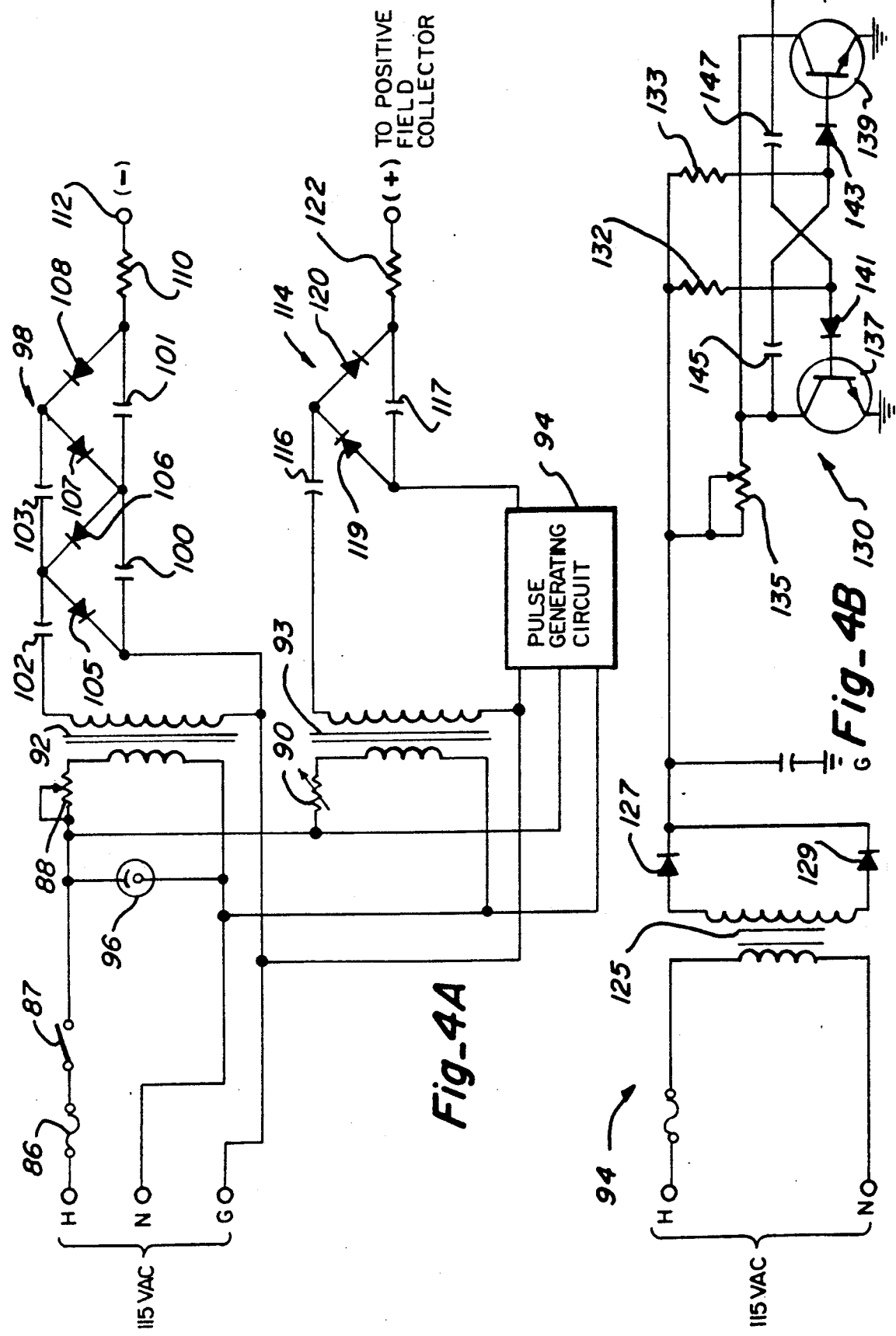

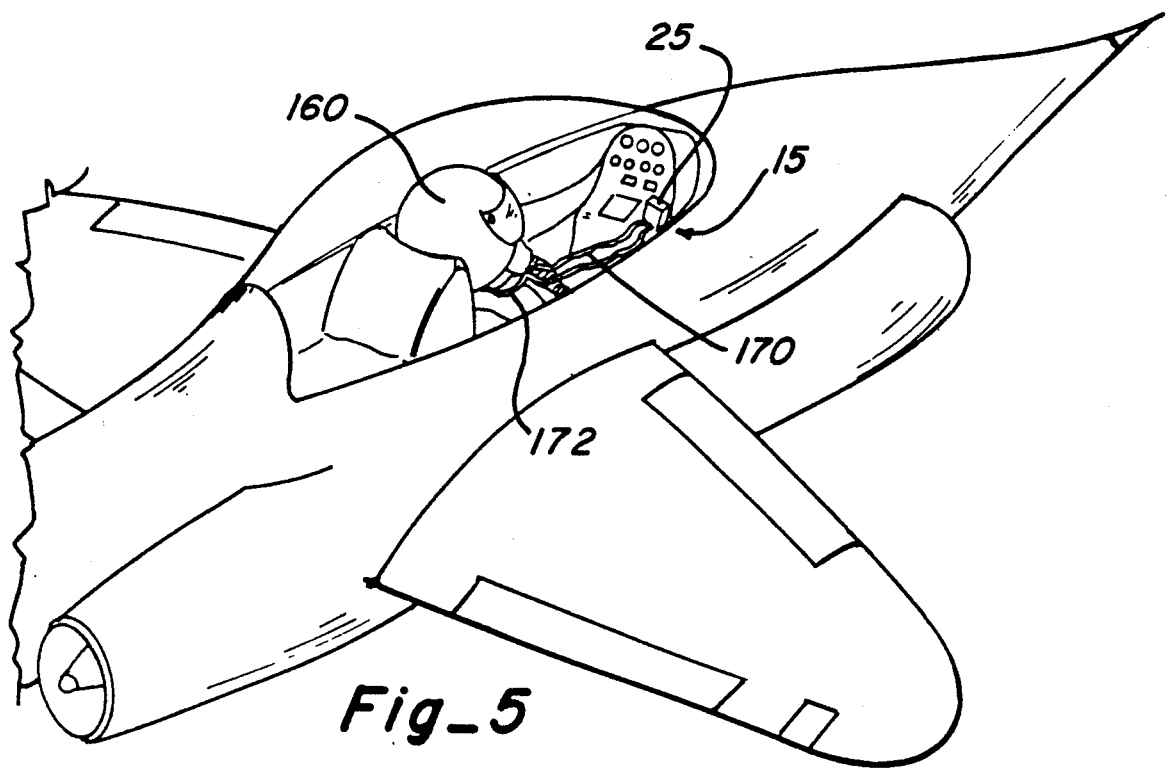
Fig_5
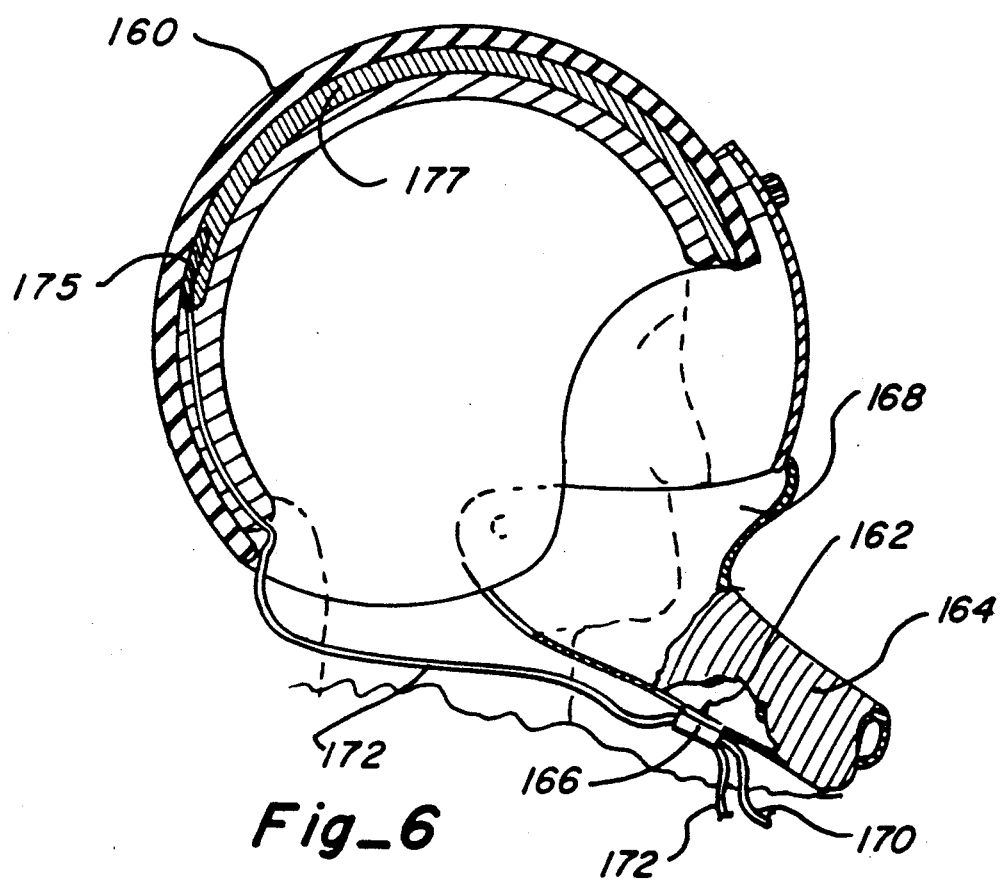
Fig_6

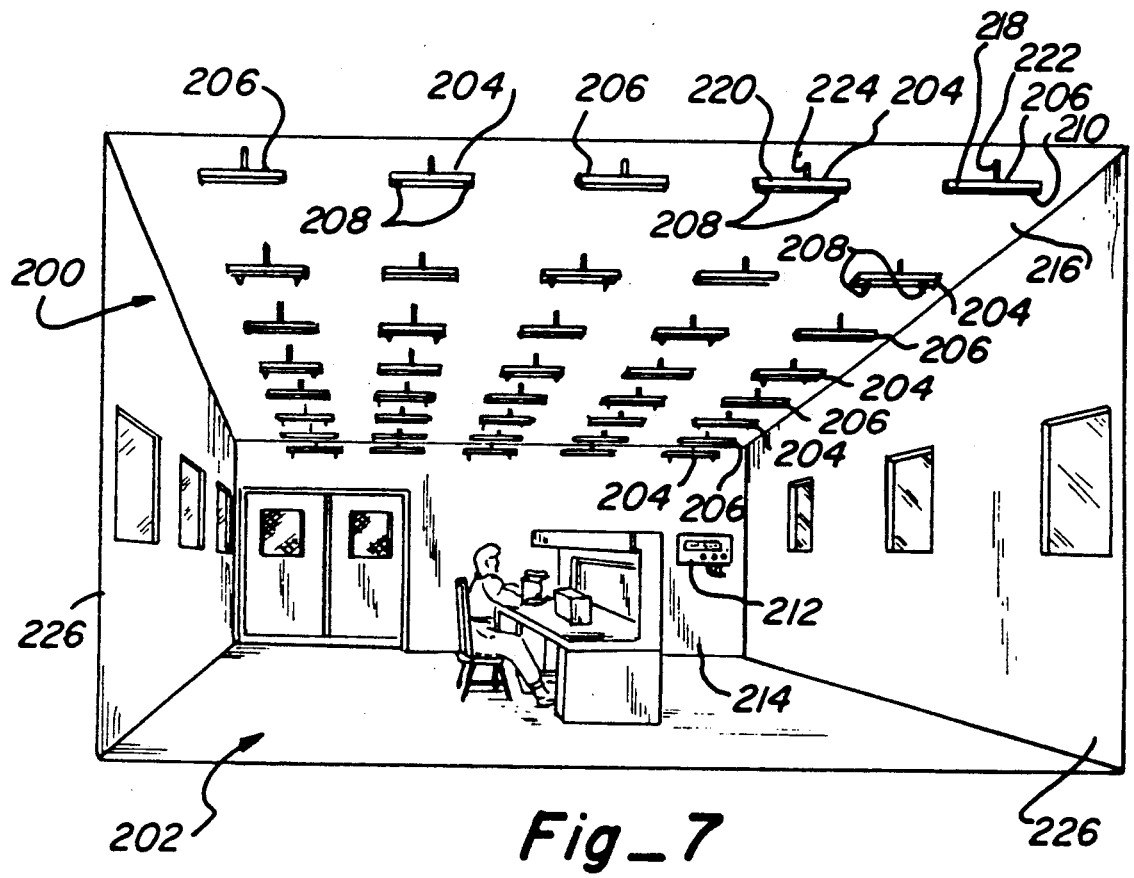
Fig_7
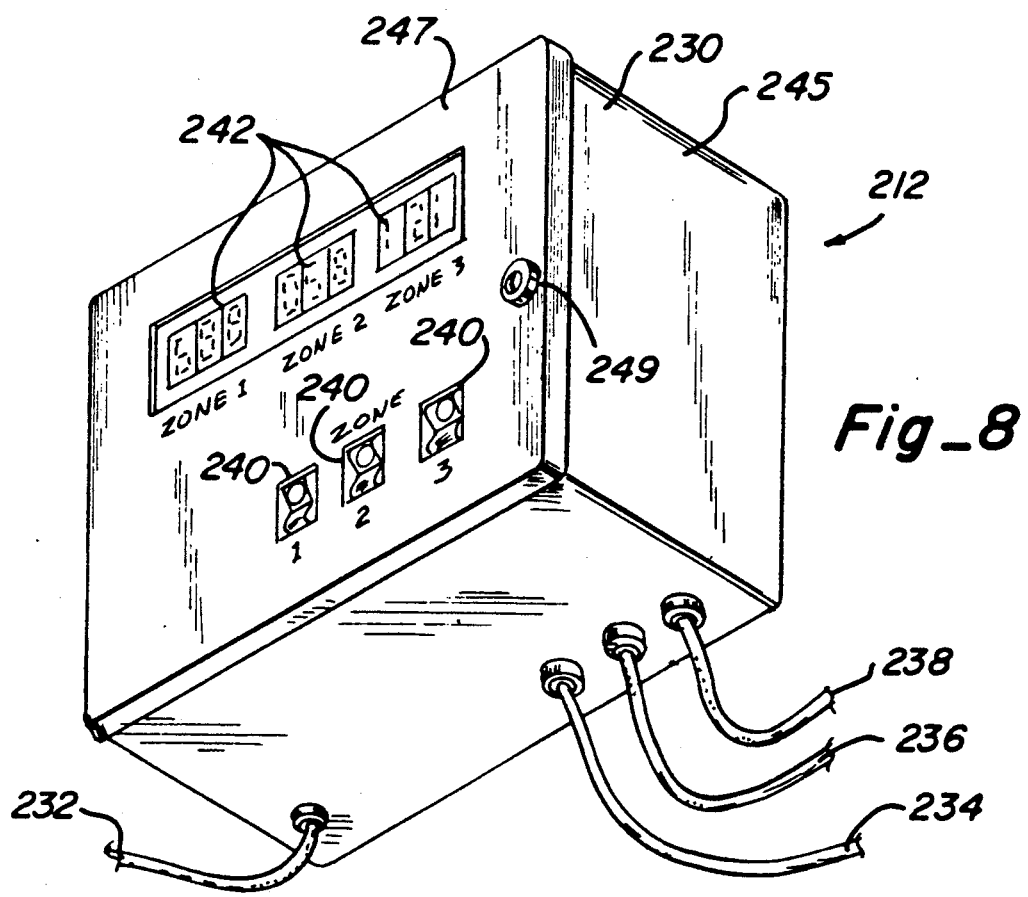
Fig_8

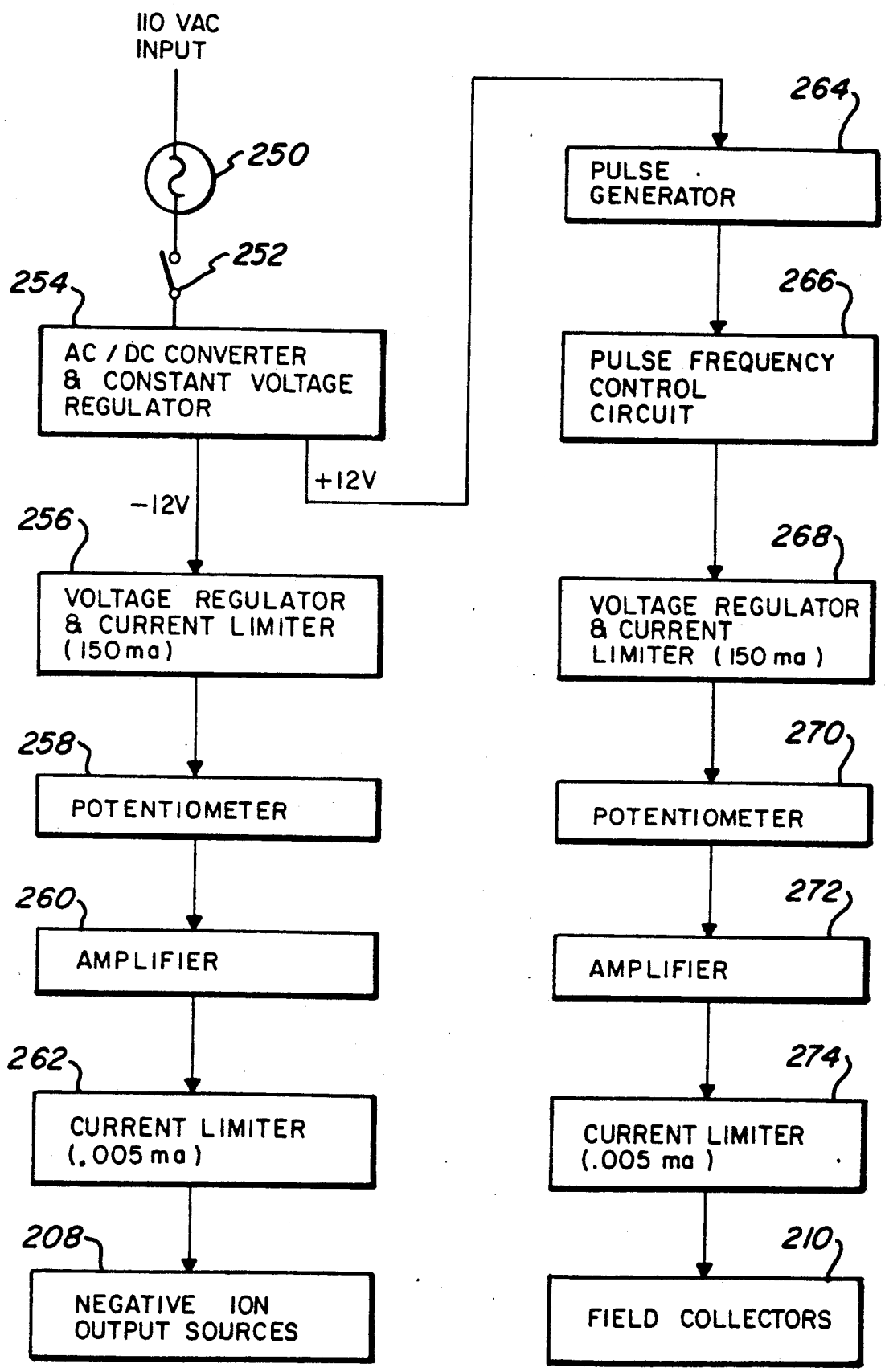
Fig_9

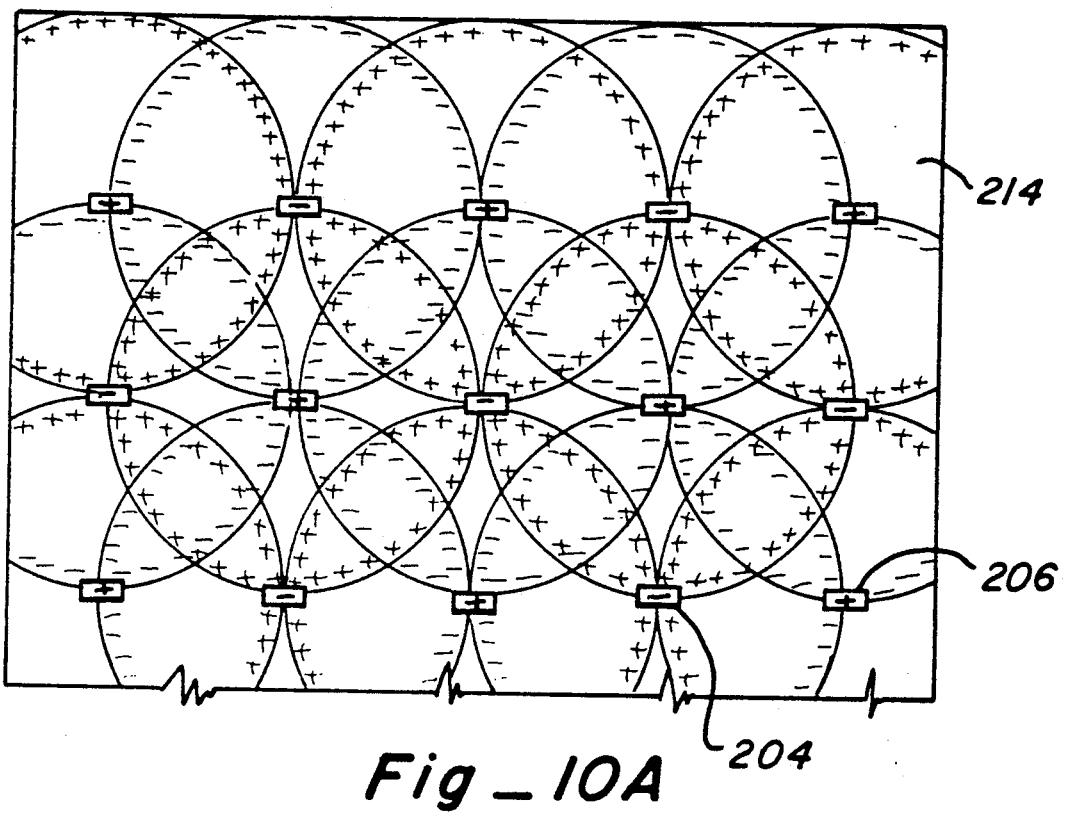
Fig_10A
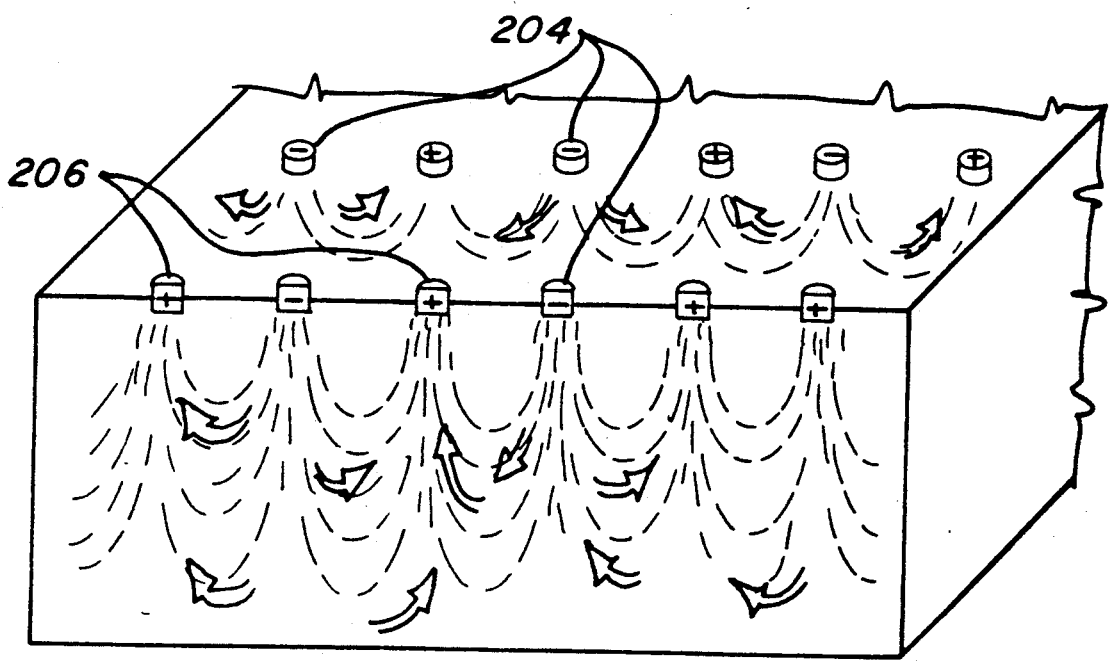
Fig_10B

APPARATUS AND METHOD FOR SELECTIVE ENVIRONMENTAL CONDITIONING OF SUBSTANTIALLY ENCLOSED AREAS

RELATED APPLICATION

This application is a continuation-in-part of copending U.S. patent application Ser. No. 138,143, filed Dec. 28, 1987 and issued on Mar. 27, 1990 as U.S. Pat. No. 4,911,737.

FIELD OF THE INVENTION

This invention relates to environmental modification apparatus and methods and, more particularly, relates to apparatus and methods for selectively supplementing ion content and electrostatic field characteristics of enclosed environments.

BACKGROUND OF THE INVENTION

Devices for ameliorating certain adverse characteristics of interior environments to enhance the well being of occupants thereof are known and have heretofore included means for generating ions and for purification of air (see for example U.S. Pat. Nos. 4,542,434, 4,528,612, 4,493,247, 4,271,452, 3,662,217, 1,167,053, and Re. 27,027).

Devices are also known for provision of an electrostatic field, and/or for establishing disturbances, or pulses, in an electrostatic field within such environments (see for example U.S. Pat. Nos. 4,271,452, 3,894,852, 3,680,281, 3,678,337, 3,662,217, 3,541,390, 3,531,150, 3,483,672, 2,184,644, 1,167,053, and Re. 27,027,).

Indoor, or enclosed, environments have long been believed to shield occupants thereof from naturally occurring and beneficial electric fields which exist near the earth from 50 to 750 volts per meter, a phenomenon known as the Faraday Cage Effect, as well as shielding the occupants from the pulsed resonance within such naturally occurring fields (commonly referred to as the Schumann Resonance). Pulsating fields are believed to have positive effects on humans and have a frequency typically in a range between 7 Hz and 32 Hz (and more commonly between 7 Hz and 10 Hz) and are now also believed to accelerate particle movement within an environment. It is also believed that some such environments become ion depleted, and are, therefore, particularly susceptible to accumulation of gaseous and particulate pollutants.

It has also been suggested that provision in an enclosed environment of negative ions may stimulate biochemical reactions and/or increase the metabolic rate of those breathing the ions, and may also reduce production of the hormone serotonin that is believed to be associated with depression and fatigue. (See Yaglow, C. P., "Are Air Ions a Neglected Biological Factor?" pp 269-279, in "The Air We Breathe—A Study of Man and His Environment", Farber, S. M. and Wilson, R.H.L. Editors, Charles C. Thomas, Publisher, Springfield, IL (1961); Soyka, Fred, "The Ion Effect", E.E.P. Dutton Publisher (1977); Assael M., Pfeifer, Y., Sulman, F. G., "Influence of Artificial Air Ionization of the Human Electroencephalogram", Department of Applied Pharmacology, Hebrew University —Hadassah Medical School and School of Pharmacy, Jerusalem, Israel (1973); and Kreuger, A. P., Strubbe, A. E., Yost, M. G. and Reed, E. J. "Electric Fields, Small Air Ions and Biological Effects" Department of Biomedical and Environmental Health Sciences and the Naval Biosciences Laboratory, School of Public Health, Earl Warren Hall, University of California, Berkely, California (1976).)

While environmental modification devices heretofore known have been provided for use in closed areas, such devices have not effectively provided in a single installation an apparatus capable of ameliorating a plurality of adverse environmental conditions experienced in enclosed environments and/or providing a combination of enhancements to the environment to offset such conditions, have not recognized the value of an apparatus which is selectively controllable and positionable to maximize beneficial effects thereof, and have often been cumbersome and/or unduly complicated to install, in many cases requiring extensive modification of the interior of such areas for application of the devices. As may be appreciated, therefore, further improvements in such devices could be utilized.

SUMMARY OF THE INVENTION

This invention provides an apparatus and method for selective conditioning of selected characteristics of substantially enclosed areas, or environments (for example rooms, vehicles including, but not limited to, ground vehicles, aircraft, spacecraft, marine craft and the like, and helmets worn by occupants and operators of such vehicles), to thereby promote removal of undesired matter from the area while more nearly establishing predetermined naturally occurring environmental characteristics therein to thus enhance the utility of the area including the performance and well being of equipment, operators and occupants of the enclosed environment.

The apparatus includes a negative ion generator, an electrostatic field generator and, in one embodiment, preferably includes a plurality of negative ion output sources and positive field collectors, with the ion output sources and field collectors being selectively positioned relative to one another to maximize the efficiency of the apparatus. The field generator includes a field pulsator, with both of the generators and the pulsator preferably being controllable and positioned to selectively determine the quantity, or concentration, and point of discharge of negative ions, the strength and distribution of the electrostatic field, and the frequency of the pulsations in the electrostatic field to thus promote a substantially constant voltage and polarity within the enclosed area so that charge differentials between units such as surfaces, devices, inhabitants and the like, and undesired matter, such as dust, particulates and the like, are minimized.

The apparatus may be permanently installed or be portable between environments, and is advantageously employed in a system for modification of interior environments including air filtration, for example, using high efficiency particulate air (HEPA) and/or activated carbon charcoal type filters.

It is therefore an object of this invention to provide an improved apparatus and method for selective conditioning of predetermined characteristics of substantially enclosed areas.

It is another object of this invention to provide an improved apparatus and method for selectively conditioning enclosed environments by providing negative ions, a positive electrostatic field, and electrostatic field pulsations within the environment.

It is still another object of this invention to provide an apparatus and method for selective environmental conditioning of enclosed areas by provision of negative ions, a positive electrostatic field grid and electrostatic field pulsations within the area, with the positions of negative ion and positive field generation being selected to maximize even distribution of negative ions and the positive field within the area.

It is still another object of this invention to provide an apparatus and method for selectively conditioning substantially enclosed environments which provides the user with the capability of selecting the quantity of negative ion output, the strength of the electrostatic field, and the frequency of the pulsations within the electrostatic field.

It is still another object of this invention to provide a compact apparatus for selectively supplementing substantially enclosed environments which is usable in vehicles such as land vehicles, aircraft, space craft, marine craft, and the like, and/or which may be used in association with the protective head gear, for example, a helmet, of an operator of such vehicles.

It is yet another object of this invention to provide an apparatus and method for selective conditioning of preselected characteristics of a substantially enclosed utilization area which provides for generation of negative ions and a pulsed positive electrostatic field within the area, with a plurality of positions in the area for generation thereof being selected so that a substantially constant polarity and voltage is maintained within the area to thereby minimize charge differentials between structural elements, units such as equipment, work surfaces and occupants, and undesired matter to thus condition the area for collection and removal of the undesired matter while more nearly establishing predetermined naturally occurring environmental characteristics therein.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate complete embodiments of the invention according to the best mode so far devised for the practical application of the principles thereof, and in which:

FIGURE 1A perspective view of a portable environmental control apparatus the control module of which is removably attachable at a preselected position in the interior of a vehicle, for example to the sun visor of an automobile, and illustrating use of the apparatus in an overall system including filtration of intake and/or recirculated air;

FIGURE 1B a front elevation view of the control module shown in FIGURE 1A;

FIGURE 1C a rear elevation view of the control module shown in FIGURE 1B shown in conjunction with the remotely positionable positive field collector used in the apparatus;

FIG. 2 is a block diagram of the components of a first embodiment of the portable environmental control apparatus of FIG. 1 which is operable from its own internal power source;

FIG. 3 is a block diagram of a second embodiment of the environment control apparatus of FIG. 1 operable from a 12 volt power supply system within the enclosed environment and including means for controlling the output of the apparatus;

FIG. 4A is a schematic view of the components of a third embodiment of the environmental control apparatus operable from a conventional 115 volt AC power source;

FIG. 4B is a schematic view of the pulsing unit of FIG. 4A;

FIG. 5 is a perspective view of the compact environmental control apparatus of this invention configured for use in association with a helmet worn by the operator of an aircraft;

FIG. 6 is a sectional view of the helmet portion of the apparatus of FIG. 5;

FIG. 7 is a perspective view of a fourth embodiment of this invention illustrating the now preferred embodiment of the invention utilized for selectively conditioning substantially enclosed areas such as a room;

FIG. 8 is a perspective view of the control module portion of the apparatus illustrated in FIG. 7;

FIG. 9 is a block diagram of the components of the apparatus of FIGS. 7 and 8; and FIGS. 10A and 10B are schematic illustrations illustrating negative ion and positive electrostatic field distribution achieved by desired placement of the apparatus shown in FIG. 7 in a room.

DESCRIPTION OF THE INVENTION

A first embodiment of the invention 15 is shown in FIGS. 1A through 1C. In FIG. 1A, apparatus 15 is shown releasably attached to sun visor 17 of automobile 19 using clip 21. Clip 21 is affixed to the housing 23 of environmental control apparatus module 25, which housing contains the electronic circuitry (preferably micro-circuits) for producing negative ions at electrodes 27 and 29 (typically needle electrodes which are conventionally mounted in housing 23) and the pulsed, positive electrostatic field emanating from field collector 31. The overall module 25 is compact, typically being, for example, approximately 4 inches long, 3½ inches wide and 1 inch thick.

Apparatus 15 is connected to the 12 volt battery of automobile 19 through the cigarette lighter housing 33 using interface 35, herein comprising lighter adapted plug 37 for linking the 12 volt supply to the circuitry of module 25 through cord 39.

Positive field collector 31, as shown in FIGURE 1C, includes electro-conductive carbon foam surface 45 within insulating dish housing 47, and maintained therein, for example, by nonconductive adhesive gel. Electro-conductive carbon foam surface 45 may be, for example, Ensolite CEC by Uniroyal. Collector 31 is connected to module 25 by signal supply lead 49 for coupling the voltage signal from the microcircuitry of module 25 to electro-conductive carbon foam surface 45 through electrode 51.

While module 25 is shown herein attached to the existing 12 volt battery of an automobile, it should be realized that the apparatus could make use of a variety of existing power sources in a variety of vehicles (for example land, marine, and air craft), and/or could make use of its own 12 volt battery pack as more fully set forth hereinbelow. In addition, while a 12 volt source is herein specified, it will be realized by those skilled in the art that the apparatus could be modified for use with power sources having different output voltages.

Housing 23 of apparatus 15 includes at the forward surface 55 thereof, on/off control 57, operational indicator lights 59 and 61 (indicator light 59 indicating that the ion generator is operational, and indicator light 61 indicating that the positive pulsed field is operational), as well as the negative ion generation electrodes 27 and 29.

By providing a module and field collector which may be selectively positionable within the particular enclosed environment, the point of generation of negative ions may be advantageously positioned to maximize intake of negative ions by a user of the device, and positioning of the positive field collector may also be advantageously selected for maximum effectiveness, for example above the head of the operator (or passenger) (using, for example, strips of the trademarked product Velcro 62 attached to dish housing 47). In addition, provisions may optionally be made for grounding of the operator and/or occupants, if desired.

If a more permanent positioning of the positive field collector 31 is desired, the field collector may be permanently installed (by use of screws, adhesives or the like) with cord 39 provided with a jack for attachment to a mating jack located in housing 23. In addition, an additional outlet receptacle 63 for provision of an additional, remote ion electrode may be provided in module housing 23. Hand-manipulable control knobs 64, 65 and 66 (as shown in FIG. 1B) may be provided at the forward surface 55 of housing 23 for adjustment of negative ion output, positive electrostatic field strength, and the frequency of pulsations provided within the field respectively (as described hereinbelow).

Air intake and/or recirculation ducts (for example duct 67) may have filters (for example filter 68) positioned therein to thereby provide filtering of particulates and gases otherwise present in the environment. The filter system is preferably a combination of a 0.3 micron high efficiency particulate air (HEPA) filter 68' and an activated carbon charcoal filter 68".

Turning now to FIG. 2, one embodiment of a circuitry for apparatus 15 is shown, with the apparatus being operable from its own 12 volt battery pack 69. The +12 DC voltage supplied from battery pack 69 is received by constant voltage regulator 70 upon activation of on/off switching mechanism 71. Constant voltage regulator 70 (for example a 12 volt Zener diode) provides a steady +12 volt signal which is received by DC step-up transformer 72, the secondary coil of which is center tapped, providing a 350 volt signal at one output and a 2,500 volt signal at the other output. The 350 volt signal is received by pulse generator 73 the output signal of which is pulsed at a frequency of about 7.830 Hz. Pulse generator 73 is connected with rectifier 74. The positive portion of the pulsed 350 volt signal is thereafter received at current limiter 75 for limiting the current of the signal to about 0.005 mA at positive field collector 31.

The 2500 volt signal from step-up transformer 72 is received at amplifier 76 where the signal is amplified providing a 3.5 KV signal which is rectified at rectifier 77. The negative portion of the signal is received at current limiter 78 (limiting signal current to 0.005 mA) and thereafter at electrodes 27 and 29 as well as auxiliary ion output interface 79.

A second embodiment of the circuitry of apparatus 15 is shown in FIG. 3 and includes interface 35 attachable to a 12 volt power source 81 already existing within the particular enclosed environment. As indicated in FIG. 3, the DC signal provided at interface 35 is coupled through switch 71 and constant voltage regulator 70 to DC step-up transformer 72 which is connected with pulse generator circuitry 73 and amplifier 76 as was previously described in FIG. 2. However, the output signals from transformer 72 are connected to potentiometers 82 and 83, potentiometer 82 allowing user regulation of the intensity of the electrostatic field produced at field collector 31, preferably within a range from 0 to 350 volts, and potentiometer 83 allowing control over voltage supplied to the negative ion output sources 27 and 29 in a range from 1.5 KV to 3.5 KV thereby allowing user regulation of the quantity of negative ions produced at the electrodes.

Pulse frequency control circuit 84 is connected between pulse generator 73 and potentiometer 83 for providing user control of the frequency of the pulses within the electrostatic field in a range from 7 to 32 Hz (preferably from 7 Hz to 12 Hz), which range corresponds with the naturally occurring pulsations in the electrostatic field surrounding the earth commonly referred to as the Schumann resonance. It is now believed that the preferable setting however will provide pulsation frequency of about 7.83 Hz.

While user controls for control of ion output, electrostatic field strength and frequency of field pulsations are shown in FIG. 3, it should be realized that control over less than all of the above parameters may be desirable in any particular embodiment of the invention, those parameters without such user control being set for a predetermined output in a desirable range as heretofore discussed.

Referring now to FIGS. 4A and 4B, the circuitry for another embodiment of the apparatus is shown for use in association with a conventional 115 volt AC power supply. The 115 volt signal is coupled through fuse 86 and switch 87 to potentiometer 88 and variable resistor 90. Potentiometer 88 is connected to step-up transformer 92 for stepping the voltage up to 1200 volts. Variable resistor 90 is connected to step-up transformer 93 for separately stepping up the voltage output from the secondary coil thereof to 1000 volts. The 115 volt signal is also provided to pulse generating circuitry 94 for providing a pulsed output having a frequency of between 7 and 12 Hz (as more fully illustrated in FIG. 4B). Indicator lamp 96 is provided for indicating operability of the apparatus upon closure of switch 87.

The output from transformer 92 is connected with amplifier and rectifier circuitry 98 for providing a rectified signal therefrom having a user controlled voltage of between 0 and −9 KV. Amplifier and rectifier circuitry 98 is a conventional circuit and includes capacitors 100, 101, 102 and 103, diodes 105, 106, 107 and 108 and resistor 110. The amplified and rectified voltage signal is supplied to negative ion output source 112 for adjustable negative ion output thereat.

The output from transformer 93 is connected to amplifier/rectifier circuitry 114, as is pulse generating circuitry 94. Amplifier and rectifier circuitry 114 includes capacitors 116 and 117 and diodes 119 and 120 in a conventional configuration, and is connected through resistor 122 to a positive field collector as previously set out herein. Variable resistor 90 enables user control over the intensity of the positive electrostatic field produced at the field collector in a range from 0 to +3.2 KV.

FIG. 4B illustrates in detail adjustable frequency pulse generating circuitry 94 overall operation of which effectively establishes a ground interrupt system for establishing and regulating pulsations in the positive electrostatic field. The 115 volt AC signal is received at step-up transformer 125 (preferably producing an output matching that of transformer 93) the opposite sides of the secondary coil of which are connected to diodes 127 and 129 for full wave rectification of the signal. The DC output from the diodes is connected to pulse producing circuit 130 which includes resistors 132 and 133 and potentiometer 135. The DC signal is received at the bases of transistors 137 and 139 through resistors 132 and 133 and diodes 141 and 143, and is received at the collectors of transistors 137 and 139 through potentiometer 135 (for control over frequency of pulsations). The emitters of transistors 137 and 139 are connected to ground. Capacitor 145 is connected between the collector of transistor 137 and the junction of the base of transistor 139 (through diode 143) and resistor 133. The out signal from circuit 130 is received at amplifier/rectifier circuitry 114 through capacitor 147.

FIGS. 5 and 6 illustrate an embodiment of apparatus 15 wherein module 25 may include circuitry substantially similar to the circuitry shown in FIGS. 2 or 3. As shown in FIG. 5, however, module 25 is used in connection with a protective head gear, for example helmet 160 (herein shown to be a helmet typical of those which may be used by aviators and the like).

As shown in FIG. 6, helmet 160 is provided with negative ion electrode 162 adjacent air intake nozzle 164, with the electrode being provided in insulating housing 166. By provision of the negative ion output at the point of attachment of nozzle 164 to mask 168, the user of helmet 160 maximizes intake of negative ions. Of course, when the apparatus of this invention is used in association with a helmet having no such air intake system and/or face mask, the position of the negative ion output electrode may still be selectively located, as set forth in FIG. 1 for example.

Signal supply line 170 is provided between electrode 162 and module 25. A second signal cord 172 from module 25 is provided at the rear of helmet 160 (and may include a jack and plug arrangement for disengagement of the line from the helmet) for connection to electrode 175 in electro-conductive carbon foam surface 177. In this fashion, the positive electrostatic field is provided at the electro-conductive carbon foam surface 177 within helmet 160. In other regards, the circuitry of module 25 is substantially similar to that shown in FIGS. 2 and 3, and provides for the output of negative ions and a positive electrostatic field which is pulsed within the 7 to 32 Hz range, and which may also include user controls for controlling the frequency of pulsations, the intensity of the electrostatic field, and the quantity of negative ion output.

FIG. 7 illustrates a fourth, and now preferred, embodiment of this invention utilized for selectively conditioning substantially enclosed areas such as room 202, which may be an office, clean room, or the like. Apparatus 200 includes a plurality of negative ion generators 204 and positive electrostatic field generators 206. The negative ion generators each include a pair of electrodes 208 spaced approximately 24 inches apart, and the electrostatic field generators 206 include field collector surfaces 210, for example elongate electroconductive carbon foam collector surfaces similar to those heretofore discussed.

Control unit 212 is mounted on rear wall 214 of room 202, and each of the electrostatic field generators 206 and the negative ion generators 204 are mounted to ceiling 216 utilizing housings 218 and 220, respectively, including mounting rods 222 and 224 for mounting the units adjacent to but spaced a short distance from ceiling 216.

While it is desirable to have the units mounted on the ceiling, the units could be mounted on side walls 226 or rear wall 214 (as well as a front wall, not shown herein) although it is preferable for the negative ion generators to be ceiling mounted in most cases.

It has been found that when the generators are mounted a preselected distance apart (preferably from 3 to 7 feet apart) and preferably with ion generators and electrostatic field generators being positioned alternately between side walls 226 and between rear wall 214 and the front wall, more even distribution of negative ions and the positive field is achieved providing a substantially constant voltage and polarity in the area thus minimizing charge differentials between structure (including walls, floors, equipment, work surfaces, people and the like) and undesired matter to be collected and removed from the room.

It has been found that positioning generators 204 and 206 closer than about 3 feet results in undesired field effects thereby reducing the concentration, and thus cleaning effect, of negative ions throughout an area, while a greater distance than about 7 feet between the units reduces the performance level of the apparatus by again negatively effecting the concentration and even distribution of ions in the field and thereby extending the period required for collection of undesired matter from the area (such as particulate matter, dust, processing by-products, and the like).

When installing the units in an area, a background reading of the ions and particulate matter to be removed in the 5 micron to 0.001 micron range is taken. Once the level of such particulates present in the area is known, the unit is calibrated to produce the desired concentration of negative ions and positive field strength, and the generators are installed in selected positions to achieve the desired evenness of distribution of the negative ions and positive electrostatic field within the area. For example, given a constant voltage, it is desirable for generators to be positioned more closely (for example, at 3 foot intervals) where there is a higher concentration, or more hazardous variety, of particulates to be removed, while the units would be spaced more widely (toward the 7 foot spacing) where less concentration of negative ions at some predetermined distance from the generators is desired, such as in offices and the like. Of course, concentration at given spacing within the range can be varied by adjusting the voltage at the outputs of the generators, the spacing of the generators or combination thereof.

When the apparatus is positioned as above described, a substantially constant polarity and voltage is selectively maintained within the area thus minimizing charge differentials between the various structural units in the area, equipment, people and the matter which is to be removed from the area. Particulates and other matter to be removed, having a smaller mass, will, upon exposure to the negative ions, attach to the ions within the positive field and be attracted to the positive field collectors 210. The particulates are felt to become polarized in this manner so that the negatively charged portion of the particles maintain an orientation toward the positive field collector surface, and in fact may form chain-like structures between themselves, thus further enhancing their movement toward the positive field collector.

As heretofore discussed, the positive field produced by the positive field generators is pulsed in the 7 to 10 Hz range, preferably at 7.83 Hz, with each of the pulsations having an intensity of approximately 150 to 200 volts (again simulating naturalistic ionic cavity field resonance). It is felt that the pulsations in the positive electrostatic field assist in exciting atomic and molecular motion and thus movement of the particles toward the positive electrostatic field collector surfaces 210. Furthermore, since the voltage pulsations are small relative to the overall positive voltage produced at the collector of the electrostatic field generator, substantially constant voltage is still selectively maintained in the area.

In addition, the overall beneficial effects heretofore set forth of reducing the so-called Faraday cage effect and reproducing more naturally occurring fields found within the earth's ionic cavity, thus offsetting the 50 to 60 Hz syndrome found in modern architecture, are provided, thus providing many of the same benefits to inhabitants of the area.

FIG. 8 illustrates control unit 212 including control unit housing 230, power supply cord 232, zone supply cables 234, 236 and 238, zone on/off switches 240 and zone indicators 242. The different zone switches, indicators and supply cables are provided so that ion production and electrostatic field generation can be controlled in different parts of an area while other areas are left uneffected (it being understood that only a single zone may be desirable in any given case, and that all of the zones, where multiple zones are provided, are controlled by the same internal circuitry).

Housing 230 includes wall mountable housing portion 245 and door unit 247 having a lock 249 therein for tamper free maintenance of door 247 on portion 245. While not shown herein, control unit 212 includes, within the housing, adjustment mechanisms for adjusting the quantity of negative ion output, strength of the positive electrostatic field and frequency of pulsations in the electrostatic field, as was set forth heretofore.

FIG. 9 is a block diagram illustrating the circuitry to be found within control unit 212. The unit is connected to a 110 volt AC power source and includes fuse 250 (for example a ½ amp fuse) and on/off switch 252. The 110 volt AC signal is coupled through fuse 250 and switch 252 with the input of AC to DC converter and constant voltage regulator 254, for example a POWER-ONE, Inc. HB12-1.7A AC to DC converter and constant voltage regulator unit, which provides a −12 volt DC and a +12 volt DC signal at its output.

The −12 volt signal output is connected to the input of voltage regulator and current regulator 256 for limiting the output signal amperage to 150 ma with an output voltage of 6 to 12 volts, depending on the particular application.

Potentiometer 258 is provided to adjust voltage to thus allow a user of the apparatus to control the quantity of ions output by the device (in a range from 500 to 5,000,000 negative ions per cubic centimeter, with the ions being in the 0.001 micron range). The signal is then amplified by amplifier 260 (for example a Murata Erie Company 7700-694-000 amplifying unit) and presented at current limiter 262 for limitation of current to 0.005 ma (as heretofore set forth) before coupling of the output signal to negative ion output sources, or electrodes, 208.

The +12 volt signal from AC to DC converter and constant voltage regulator 254 is provided at the input to pulse generator circuitry 264 which is connected to pulse frequency control circuit 266 (as previously discussed heretofore) for providing frequency controllable pulsations in the positive field. The signal from pulse frequency control circuit 266 is provided at the input of voltage regulator and current limiter 268 for regulating the voltage at 6 or 12 volts, as desired, and limiting the current to 150 ma.

The signal at the output of voltage regulator and current limiter 268 is coupled with the input of potentiometer 270 to provide user control over the intensity of the positive electrostatic field in a range between 6 and 18 kilovolts at the output of amplifier 272 (amplifier 272 being, for example, a Murata Erie 7700-327-000 amplifier). Amplifier 272 is connected to current limiter 274 for limitation of the current to 0.005 ma (current limiters 262 and 264 being substantially similar). The output signal therefrom is then coupled with field collectors 210.

FIGS. 10A and 10B are schematic illustrations of the distribution of ions within an area such as room 214, and illustrate the conical distribution of the negative ions and positive fields within the room (as shown in FIG. 10B) and the overlap of the zones of influence of the positive electrostatic fields and negative ion distribution radii to thus achieve an overall even distribution in the area of both the positive electrostatic field and negative ions.

As may be appreciated from the foregoing, this invention provides an improved apparatus and method for selective environmental conditioning of substantially enclosed areas such as vehicles, offices, clean rooms, and the like, which promotes removal of undesired matter, such as particulate matter, from the area while more nearly establishing predetermined natural occurring environmental characteristics therein to thus enhance the performance and well being of occupants and equipment therein. The apparatus includes negative ion generators and positive electrostatic field generators positioned to achieve the most advantageous distribution of negative ions in a positive electrostatic field, with the positive electrostatic field being pulsed in a range from 7 to 10 Hz, preferably 7.83 Hz. Controls are provided within the unit for user control within predetermined parameters of one or more of the quantity of negative ions generated and the intensity of, and frequency of pulsations in, the electrostatic field.

What is claimed is:

1. An apparatus for selective conditioning of preselected characteristics of a substantially enclosed utilization area to promote removal of undesired matter from the area while more nearly establishing predetermined naturally occurring environmental characteristics therein, said area being formed by structure having inwardly facing surfaces, said apparatus comprising:

negative ion generating means for generating a selected quantity of negative ions within the area;

positive electrostatic field establishing means including field collector means positioned adjacent to, and spaced a preselected distance from, said negative ion generating means in said area, said positive field establishing means for generating a selected field intensity within the area and further including pulse establishing means for establishing pulsations having a selected frequency in said positive electrostatic field; and control means for controlling selection of said quantity of ions generated by said ion generating means and selection of said intensity of said electrostatic field generated by said electrostatic field establishing means independently of one another.

2. The apparatus of claim 1 wherein said apparatus includes a plurality of negative ion generating means, each of said negative ion generating means being spaced a preselected distance from one another in said area.

3. The apparatus of claim 1 wherein said positive electrostatic field establishing means includes a plurality of positive field collector means each of which is positioned adjacent to, and spaced a preselected distance from, said negative ion generating means in said area.

4. The apparatus of claim 1 wherein said control means includes frequency control means for controlling the frequency of said pulsations established in said positive electrostatic field by said pulse establishing means.

5. The apparatus of claim 1 further comprising first housing means for housing said negative ion generating means, second housing means for housing said field collector means of said positive electrostatic field establishing means, and third housing means for housing said control means, and wherein said preselected distance between said negative ion generating means and said field collector means of said positive electrostatic field establishing means is between about three feet and seven feet.

6. An apparatus for selective conditioning of preselected characteristics of a substantially enclosed utilization area having units therein to promote removal of undesired matter from the area while more nearly establishing predetermined naturally occurring environmental characteristics therein, said area being formed by structure including a ceiling structure and a plurality of inwardly facing surfaces, said apparatus comprising:

a plurality of negative ion generating means for generating a selected quantity of negative ions within the area, each of said negative ion generating means being spaced a preselected distance from one another in said area adjacent to said ceiling structure thereof;

positive electrostatic field establishing means including a plurality of positive field collector means each of which is positioned adjacent to, and spaced a preselected distance from, different ones of said plurality of negative ion generating means in said area, said positive field establishing means for generating a selected field intensity within the area and further including pulse establishing means for establishing pulsations having a selected frequency in said positive electrostatic field; and control means for controlling selection of said quantity of ions generated by said ion generating means and selection of said intensity of said electrostatic field generated by said electrostatic field establishing means independently of one another.

7. The apparatus of claim 6 wherein said plurality of positive field collector means of said positive electrostatic field establishing means is positioned adjacent to said ceiling structure in said area.

8. The apparatus of claim 6 wherein each of said plurality of negative ion generating means includes a plurality of electrodes for generating negative ions therefrom.

9. The apparatus of claim 6 wherein each of said positive field collector means of said positive electrostatic field establishing means includes an elongate electroconductive carbon foam collector surface.

10. The apparatus of claim 6 wherein said structure includes side wall structures and wherein said plurality of negative ion generating means and said positive field collector means of said positive electrostatic field establishing means each include mounting means for mounting said negative ion generating means and said positive field collector means adjacent to and spaced a short distance from said ceiling structure, said negative ion generating means and said positive field collector means being mounted so that said negative ion generating means and positive field collector means are alternately arranged between said side wall structures of said structure forming said area.

11. The apparatus of claim 6 wherein said control means includes frequency control means for selectively controlling the frequency of pulsations established in said positive electrostatic field by said pulse establishing means.

12. A method for selective conditioning of preselected characteristics of a substantially enclosed utilization area to promote removal of undesired matter from the area while more nearly establishing predetermined naturally occurring environmental characteristics therein, said area being formed by structure having inwardly facing surfaces, said method comprising:

generating a selected quantity of negative ions within said area from a plurality of preselected spaced first positions in said area;

generating a positive electrostatic field having a selected intensity in said area from a plurality of preselected second positions in said area, said second positions being adjacent to, and spaced a preselected distance from, each of said first positions;

establishing pulsations having a selected frequency in said positive electrostatic field; and selecting said quantity of negative ions and said intensity of said positive electrostatic field independently of one another.

13. The method of claim 12 wherein said structure forming said area includes ceiling structure and side wall structures, and wherein said first and second positions are adjacent to said ceiling structure, and wherein said first and second positions are alternatively arranged between said side wall structures.

14. The method of claim 13 wherein said preselected distance is between about three feet and seven feet.

15. The method of claim 12 wherein said spaced first positions each include first and second spaced ion generating points, and wherein said second position has an elongate electrostatic field collector positioned thereat.

16. The method of claim 12 further comprising the step of selectively controlling the frequency of said pulsations established in said positive electrostatic field.

17. The method of claim 12 wherein said selected frequency is about 7.83 Hz.

* * * * *